United States Patent [19]

Gergely et al.

[11] Patent Number: 5,587,179
[45] Date of Patent: Dec. 24, 1996

[54] PHARMACEUTICAL FORMULATION IN THE FORM OF AN EFFERVESCENT AND/OR DISINTEGRATING TABLET OR OF INSTANT GRANULATE, AND PROCESS FOR THEIR PREPARATION

[75] Inventors: Gerhard Gergely; Thomas Gergely; Irmgard Gergely, all of Vienna, Austria

[73] Assignee: Gerhard Gergeky, Austria

[21] Appl. No.: 256,503

[22] PCT Filed: Jan. 12, 1993

[86] PCT No.: PCT/EP93/00055

§ 371 Date: Jul. 13, 1994

§ 102(e) Date: Jul. 13, 1994

[87] PCT Pub. No.: WO93/13760

PCT Pub. Date: Jul. 22, 1993

[30] Foreign Application Priority Data

Jan. 13, 1992 [EP] European Pat. Off. .............. 92100441

[51] Int. Cl.$^6$ ...................................................... A61K 9/46
[52] U.S. Cl. ..................... 424/466; 424/489; 424/484; 424/486; 424/488
[58] Field of Search .................... 424/466, 486, 424/464, 465, 488; 514/965, 964

[56] References Cited

U.S. PATENT DOCUMENTS

| | | | |
|---|---|---|---|
| 4,289,751 | 9/1981 | Windheuser | 424/35 |
| 4,539,198 | 9/1985 | Powell et al. | 514/960 |
| 4,704,284 | 11/1987 | Betty et al. | 424/469 |
| 4,832,956 | 5/1989 | Gergely et al. | 424/466 |

FOREIGN PATENT DOCUMENTS

| | | |
|---|---|---|
| 0103387 | 3/1984 | European Pat. Off. . |
| 0181564 | 5/1986 | European Pat. Off. . |
| 0208144 | 1/1987 | European Pat. Off. . |
| 0219458 | 4/1987 | European Pat. Off. . |
| 0393909 | 10/1990 | European Pat. Off. . |
| 2160100 | 12/1985 | United Kingdom . |
| 8701936 | 4/1987 | WIPO . |

*Primary Examiner*—Thurman K. Page
*Assistant Examiner*—P. Webber
*Attorney, Agent, or Firm*—Ostrolenk, Faber, Gerb & Soffen, LLP

[57] ABSTRACT

The pharmaceutical formulation in the form of an effervescent and/or disintegrating tablet or of instant granules contains at least one active ingredient having an irritating taste and at least one matrix which delays the release of the active ingredient and is present as an intimate mixture with the active ingredient particles or covers said particles and is applied to a carrier. The formulation releases at most 65%, preferably at most 50%, of the active ingredient in aqueous solution at room temperature within about 2 min but more than 70%, preferably at least 80%, of the active ingredient within max. 20 min, preferably max. 15 min, in 0.1N HCl at 38° C. The matrix preferably contains at least one fatty ester and/or one wax, preferably having a melting point between 30° and 45° C., in particular between 32° and 35° C., and/or at least one cellulose derivative and/or at least one polymethacrylate. In particular, the active ingredient is present in an amount of less than 60 mg, preferably less than 10 mg, and the matrix is present in an amount of 1 to 10, preferably 3 to 5, times the amount of active ingredient per tablet or granule dose. For the treatment of diarrhoea by means of loperamide, the matrix additionally contains a mixture which serves to compensate for the electrolyte loss in the body and an amount of alkali metal and/or alkaline earth metal salts, preferably of organic salts, and of chlorides.

17 Claims, No Drawings

PHARMACEUTICAL FORMULATION IN THE FORM OF AN EFFERVESCENT AND/OR DISINTEGRATING TABLET OR OF INSTANT GRANULATE, AND PROCESS FOR THEIR PREPARATION

The invention relates to a pharmaceutical formulation in the form of an effervescent and/or disintegrating tablet or of instant granules, containing at least one active ingredient having an irritating taste and at least one matrix which delays the release of the active ingredient. The invention also relates to a process for the preparation of such a pharmaceutical formulation.

The preparation of instant systems, such as, for example, effervescent tablets and granules, and soluble systems has so far been restricted to active ingredients having a neutral taste. However, it is increasingly being required also to incorporate into soluble instant systems active ingredients which irritate the taste nerves, particularly when they have a very bitter taste. Examples of these are dimenhydrinate, codeine, loperamide, diclophenac, acelastin, loperamide oxide, domperidone, cisaprid, paracetamol and many others.

Another difficulty in the incorporation of such active ingredients is the fact that in the case of effervescent tablets, which generally weight 2–4 g, the ratio of active ingredient to effervescent granules may be up to 1:1000. Apart from the problem of the bitterness, this also gives rise to the problem of the uniform distribution of the active ingredient, which is difficult to solve.

To mask an active ingredient which has a slightly bitter but essentially "prickling" taste, namely ibuprofen, EP-B1-0181564 has already proposed coating the active ingredient with fumaric acid and hydrocolloids. In aqueous solution, the acidic taste masks the slightly bitter one; the hydrocolloids also help in this masking but essentially serve as suspension excipients. In any case, this coating cannot prevent the release of the ibuprofen or other active ingredients having a strong irritating taste during the few minutes for which a prepared solution stands before it is drunk.

It has also been proposed for chewable tablets, for example in EP-A-212 641, to mask dimenhydrinate—one of the stated substances having an irritating taste—by incorporation in a polymethacrylate matrix, for example in Eudragit S, which is also said to be successful. However, it was not taken into account that Eudragit S is poorly soluble in an acidic medium and therefore releases the active ingredient only in the intestine, which may be acceptable for dimenhydrinate (only in isolated cases) but not for active ingredients which are intended to be released in the acidic medium of the stomach. This solution alone is therefore also unsatisfactory, for example, for effervescent tablets.

The object is achieved only if the matrix is present as an intimate mixture with the active ingredient particles and covers said particles and is applied to a carrier, the formulation releasing at most 65, preferably at most 50, % of the active ingredient within about 2 min in aqueous solution at room temperature but more than 70, preferably at least 80, % of the active ingredient within max. 20, preferably max. 15, min in 0.1N HCl at 38° C.

The above-mentioned problems can therefore surprisingly be solved for the first time in particular if the matrix contains at least one fatty ester and/or one wax, preferably having a melting point between 30° and 45° C., in particular between 32° and 35° C. It may contain, for example, at least one cellulose derivative, preferably hydroxypropylmethylcellulose phthalate (HPMCP), cellulose acetate phthalate (CAP), cellulose acetate trimellitate (CAT) or cellulose acetobutyrate (CAB), in particular at least one polymethacrylate, preferably Eudragit L alone or as a mixture with Eudragit S.

The carrier is chosen in particular from at least one of the substances mannitol, sorbitol, sucrose, lactose, Aerosil, starch and polyvinylpyrrolidone, or from one or more components of the effervescent system, such as, in particular, an edible, organic acid, for example alginic acid, citric acid, tartaric acid or adipic acid, or at least one alkali metal and/or alkaline earth metal carbonate and/or bicarbonate.

The active ingredient—which in particular has an irritating taste and is soluble in organic solvents or solvent mixtures, for example in an alcohol, a ketone or a chlorinated hydrocarbon—is present in an amount of less than 60 mg, preferably less than 10 mg, and the matrix is present in an amount of 1 to 10, preferably 3 to 5, times the amount of active ingredient per tablet or granule dose.

For an active ingredient for the treatment of diarrhoea, such as, for example, loperamide, the formulation additionally contains a mixture which serves to compensate the electrolyte loss in the body and an amount of alkali metal and/or alkaline earth metal salts, preferably of organic salts, and of chloride.

In the process according to the invention, the active ingredient together with the matrix is dissolved in a common solvent—preferably at slightly elevated temperature—and the solution is uniformly applied to 10–50, preferably 20–40, parts by weight (based on 1 part by weight of the sum of active ingredient and matrix) of a neutral carrier and is dried. The granules obtained are then mixed with the remaining effervescent and/or disintegration components and flavours and the like and if necessary pressed to give tablets.

The invention is suitable in particular for formulations with very low active ingredient doses, for example less than 50, in particular less than 10, mg per tablet or sachet.

The process is based essentially on the fact that the active ingredient is dissolved mainly in organic solvents together with a water-insoluble or poorly water-soluble substance, such as, for example, a cellulose derivative and/or a fatty ester or wax, for example a glyceride of saturated fatty acids, which may be melted beforehand, dissolution in any case preferably being effected at about 38° to 40° C. This solution is then distributed over a carrier and the solvent is evaporated. The carrier may be on the one hand a neutral carrier, such as mannitol, sorbitol, sucrose or lactose, or, on the other hand, Aerosil or rice starch. On the other hand, however, individual parts of the effervescent system or said system as a whole may act as a carrier, for example alginic acid, citric acid, alkali metal bicarbonates, alkali metal carbonates, etc.

The active ingredient is then present, in an easily distributable manner, either on the effervescent system, on a part thereof or on a neutral carrier, but is embedded in a cellulose derivative and/or in a glyceride of saturated fatty acids, which is formulated so that the release of the active ingredient meets the conditions according to the invention, i.e. in particular is released for the most part only at elevated temperatures in the stomach or, in specific desired cases, can be absorbed only on passage through the intestinal tract.

Possible matrix materials—in particular in combination with fatty esters or waxes—are cellulose acetate phthalate (CAP), cellulose acetate trimellitate (CAT) and cellulose acetobutyrate (CAB). Ideal for the purpose according to the invention is any mixture, for example also of soft and hard paraffins, or of corresponding synthetic products, which dissolves only slightly if at all after 2 min at pH>3–4 and room temperature but rapidly and substantially after 15 min at pH<2–3 and 38° C., if necessary also a polymethacrylate (mixture).

The active ingredient which is embedded in and distributed over the carrier surface in the matrix is present as a suspension in very finely divided form after dissolution of the effervescent system and of the carrier. If Aerosil is present as the carrier, it does not dissolve in the effervescent system. However, masking of the taste is clearly achievable by the very finely divided, suspended but embedded form during the dissolution and during drinking, without the particles containing the active ingredient adhering to the edge of the glass. Owing to the high adsorptivity, it is also possible to manage with substantially smaller weights—as will be shown subsequently in the Examples—than when, for example, mannitol or the like act as carriers.

On the other hand, the system according to the invention does not result in the otherwise usual retardation of in general several hours; instead, the active ingredient is released relatively rapidly, i.e. beginning at the earliest after 2 to 4 min in the effervescent system and only in part, but no later than after 10, in extreme cases 15 to 20, minutes but then substantially, in the gastric or intestinal tract. This clearly distinguishes the invention from conventional sustained-release products. The purpose of these is to achieve delayed active ingredient release over several hours so that a longer action period is achieved with a single dose.

Fatty esters are incorporated mainly at temperatures which are above the melting point. For example, the substances dissolved in organic solvents are mixed with the molten fatty glyceride, and this finely divided complex is taken up in Aerosil. The solvent is then evaporated, and the dried free-flowing product is added to an effervescent mixture, or it is applied, together with the solvent, to the effervescent mixture and is evaporated there.

This results in an enhanced masking of the taste as well as an accelerated release in the stomach, since the fatty glycerides melt and immediately release the total complex at the elevated temperature.

Most substances having an irritating taste, in particular the bitter substances, have a "perception threshold". In the case of loperamide, for example, half a milligram is not yet found to be bitter, and the bitterness is still tolerable in the case of one milligram but most people find it intolerable at 2 mg.

According to the invention, systems are now proposed with which the active ingredient is released, immediately on effervescence, in a portion which at most is just tolerable; the remaining amount is then released after a very long delay, or release takes place as a result of the pH and temperature conditions prevailing in the gastric or intestinal tract.

EXAMPLE 1:

Dimenhydrinate, too, can be processed with mixtures of Eudragit L and Eudragit S in a similar manner. However, to avoid slowing down the release excessively, it is possible in this case also to incorporate water-soluble substances which, so to speak, perforate the resulting polymeric inclusion product. This makes it possible for the active ingredient to be dissolved away more easily even before the matrix itself has completely dissolved.

2 parts by weight of dimenhydrinate are dissolved with 3 parts by weight of Eudragit L and 3 parts by weight of Eudragit S in a mixture of 35 parts by weight of alcohol and 10 parts by weight of isopropanol. Furthermore, depending on the desired release, 1 to 3 parts by weight of xylitol or gluconic acid delta-lactone are also dissolved in the solution. It is applied to 200 parts by weight of sorbitol and freed from the solvent at 60° C.—preferably while stirring in vacuo.

This intermediate which contains about 5% by weight of active ingredient is now introduced into an effervescent system, the effervescent suspension formed having a neutral taste in spite of the extremely bitter taste of the dimenhydrinate.

To achieve better solubility or suspension of the active ingredient, sodium chloride or gluconic acid delta-lactone or citric acid can also be introduced into the solution (about 10 to 40% by weight, based on the amount of Eudragit used), in order to make the system more permeable. In specific cases, it is also possible to dope the coating layer with alkali metal carbonates or bicarbonates, which react with acids and thus perforate the mask and make it more permeable.

EXAMPLE 2:

The procedure is as in Example 1, except that 20 parts by weight of dimenhydrinate are mixed with 5 parts by weight of Eudragit L and 50 parts by weight of Witepsol H32 and are applied to 30 parts by weight of Aerosil. The release at room temperature after 2 min is even slower, and that at 38° C. in simulated gastric fluid is accelerated.

EXAMPLE 3:

Loperamide used for the treatment of diarrhoea. In the case of diarrhoeas, it is appropriate also to consume specific electrolyte-containing liquids simultaneously or afterwards in order to compensate the electrolyte and water loss in the body. However, the obvious idea of combining loperamide with such drinks has been unsuccessful to date owing to the extreme bitterness of the active ingredient. Here too, it was found that an optimal supply of electrolytes—the supply of sodium, potassium, calcium and magnesium ions and also of sodium chloride being important—can be achieved via an electrolyte effervescent tablet which preferably has the following composition:
2 parts by weight of loperamide are dissolved with 1.5 parts by weight of Eudragit L in a mixture of equal amounts by weight of alcohol, acetone and isopropanol at 40° C. and are applied to 200 parts by weight of sorbitol. This is preferably carried out in vacuo while stirring; drying is then carried out. The resulting granules are mixed with an effervescent system having the following composition:
153 parts by weight of potassium bicarbonate (equivalent to 60 mg of K)
50 parts by weight of calcium carbonate (equivalent to 20 mg of Ca)
150 parts by weight of sodium carbonate (equivalent to 65 mg of Na)
565 parts by weight of sodium bicarbonate (equivalent to 220 mg of Na)
165 parts by weight of sodium chloride (equivalent to 100 mg of Cl)
91 parts by weight of magnesium oxide (equivalent to 50 mg of Mg)
2180 parts by weight of citric acid The prepared mixture may also be provided with suitable sweeteners and flavours and either filled into sachets or pressed to give tablets which contain 2 mg of loperamide per tablet. If the latter is intended, it is advantageous to proceed according to one of the processes described in CH-A-662926 or EP-A-272312, the content of which is considered to be disclosed for the purpose of the present description.

EXAMPLE 4: Comparison of various matrix and carrier materials:

In the following Examples, the amounts are stated in mg per tablet. In all cases, 2 mg of loperamide are dissolved together with the matrix material in 30 mg of a mixture of equal amounts of alcohol, acetone and isopropanol at about 40° C. and are applied to the carrier. This is preferably carried out in vacuo while stirring; drying is then carried out. The resulting granules are mixed with an electrolyte effervescent system having the following composition:
165 of sodium chloride
149 of potassium bicarbonate
154 of calcium lactate
333 of magnesium citrate
722 of sodium bicarbonate
500 of glucose
1900 of citric acid
Since glucose is also intended to be present in the tablet, the calcium and magnesium salts are incorporated in the form of organic salts for stability reasons.

When release after 2 minutes or after 15 minutes is mentioned in the preceding and the following Examples, this is always to be understood as follows:
2 min: 2 tablets are dissolved in 200 ml of $H_2O$ at room temperature; after 2 min, 50 ml of the solution are diluted with 50 ml of $H_2O$ and filtered; the filtrate is investigated to determine the content of released active ingredient (in %).
15 min: 2 tablets are dissolved in 200 ml of 0.1N HCl (simulated gastric fluid) at 38° C. and kept at this temperature for 15 min; 50 ml of the solution are then diluted with 50 ml of 0.1N HCl and filtered; the filtrate is investigated to determine the content of released active ingredient (in %).

Negative Examples:

It has been found that Eudragit S alone, which dissolves above pH 7, or HPMCP (hydroxypropylmethyl-cellulose phthalate) provides good masking (release after 2 min only 8.15% depending on carrier, the type of which gives very different results in some cases) but releases too little (12–50%) in acidic gastric fluid even after 15 min; the main amount of the active ingredient is released only in the alkaline intestinal environment.

Mixtures of Eudragit S with Eudragit L and/or HPMCP exhibit slightly better behaviour but are still inadequate. Furthermore, the attempt to perforate the matrix of Eudragit S by means of varying amounts of soluble substances in the matrix in order to achieve better release does not result in the desired success.

Eudragit E alone, which is acid-soluble, releases 75–90% of the active ingredient after only 2 min and is therefore unsuitable. Even when mixed with other Eudragits, the release after 2 min is still too high.

Eudragit L alone dissolves at a pH above 5.5; the effect is very dependent on the amount; 2–3 of Eudragit L release only 50–60% even after 15 min.

Positive Examples:

A substantial improvement in the achievement of the object of the invention can surprisingly be obtained—as already mentioned above—by means of fatty esters, in particular by glycerides of saturated fatty acids (hard fat, e.g. Witepsol H32$^{(R)}$, registered trade mark of Dynamit Nobel, abbreviated to "Wi 32" below) which melt below 45° C., preferably below 35° C., preferably in combination with the above-mentioned matrix materials, in particular cellulose derivatives, if necessary also polymethacrylates, such as, for example, Eudragit L (abbreviated to "Eu L" below). Fatty esters or waxes or stearic acid alone also act in the sense according to the invention but still not optimally. They must be used in relatively large amounts, which presents no problems for solid oral dosage forms. In aqueous suspensions, active ingredient particles masked in this manner tend to float or sink, although it may be possible to control this.

Furthermore, it is known that the melting point can also be depressed by emulsifiers, such as, for example, mygliol or lecithins. These also act as suspension excipients, as do propylene glycol (abbreviated to prop.glyc." below), polysorbate (Tween$^{(R)}$), alkylaryl polyglycol ethers (Eumulgin$^{(R)}$), etc.

| Example | Carrier | Matrix | 2 min | 15 min |
|---|---|---|---|---|
| 4.0 | 200 mannitol | 10 Wi 32<br>0.1 DOSS | 50 | 90 |
| 4.1 | 200 mannitol | 7.5 Wi 32<br>2 HPMCP | 40 | 92 |
| 4.2 | 200 mannitol | 7.5 Wi 32<br>2 CAT<br>0.375 Eumulgin | 47 | 92 |
| 4.3 | 200 mannitol | 7.5 Wi 32<br>2 Aerosil<br>2 Eu L | 39 | 100 |
| 4.4 | 50 rice starch | 7.5 Wi 32<br>2 Eu L | 49 | 91 |
| 4.5 | 20 Aerosil | 7.5 Wi 32<br>2 Eu L<br>0.075 Tween | 47 | 98 |
| 4.6 | 15 Aerosil<br>5 rice starch | 7.5 Wi 32<br>2 Eu L | 62 | (*)94 |
| 4.7 | 20 Aerosil | 5 Wi 32<br>3 Eu L<br>0.05 prop.glyc. | 50 | 100 |
| 4.8 | 50 alginic acid | 5 Wi 32<br>3 Eu L<br>0.05 prop.glyc. | 36 | 86 |
| 4.9 | 100 rice starch | 5 Wi 32<br>3 Eu L<br>0.05 prop. glyc. | 33 | 93 |
| 4.10 | 200 sucrose | 5 Wi 32<br>1.5 Eu L | 38 | 85 |
| 4.11 | 200 citric acid | 5 Wi 32<br>1.5 Eu L | 45 | 92 |
| 4.12 | 20 Aerosil | 5 Wi 32<br>3 HPMCP | 60 | 96 |
| 4.13 | 200 sorbitol | 1.5 Eu L | 55 | 70 |
| 4.14 | 3379 electrolyte effervescent system | — | — | — |

(*)First introduce the Aerosil in the solution and then add rice starch; now tastes very slightly bitter.

As can be seen from Examples 4.10 and 4.11, in the case of relatively freely soluble carriers, such as sucrose or citric acid, the amount of Eudragit used as a carrier in the case of Aerosil can be considerably reduced, namely to half, in order to achieve the same release.

1.5 of Eudragit L alone releases 55% after 2 min and is thus at the upper tolerance limit; after 15 min, however, only 70% of the active ingredient has been released, which corresponds to a lower tolerance limit.

Hydrogenated castor oil (Cutina HR$^{(R)}$, in particular for formulations without an effervescent system), hydrogenated arachis oil (oleum arachidis hydrogenatum), cocoa butter (predominantly oleopalmitostearin), cetaceum (spermaceti= ethyl palmitate), glyceryl monodistearate [sic] (e.g. Imwitor$^{(R)}$ 900), polyoxyethylene palmirate, triglycerides of mixed fatty acids or polyethylene glycols act very similarly to Witepsol$^{(R)}$: 5 mg of each of these with 3 mg of Eudragit L on 20 mg of Aerosil release 40–60% of the active ingredient after 2 min and 70–96% thereof after 15 min.

As can be seen from Example 4.14, under certain circumstances it is also possible to dispense with masking in the case of loperamide when a large amount of an electrolyte effervescent system is used.

EXAMPLE 5:

Diclophenac sodium is very freely soluble in water. 1 part by weight thereof is dissolved in 7.5 parts by weight of water, and the solution is applied to 5 parts by weight of alginic acid in a container with a stirring and kneading mechanism at 30°–60° C. 0.3 part by weight of citric acid powder is then added. Here, the alginic acid acts both as a carrier and—on the particle surface—as a matrix; a free-flowing powder is formed. This is dried to a residual moisture content of less than 1%, preferably in vacuo, and is sieved through a 0.5 mm sieve and added to a conventional effervescent mixture.

If 25 mg of diclophenac sodium are to be added, for example, to 2 to 4 g of such an effervescent mixture, 157.5 mg of the diclophenac complex prepared according to the invention and having a neutral taste are required, an amount which can be readily uniformly distributed in a well designed effervescent mixture. After dissolution, it has a neutral taste, whereas diclophenac sodium has an extremely bitter taste.

EXAMPLE 6:

The procedure is as in Example 5, except that 25 parts by weight of diclophenac sodium are dissolved with 5 parts by weight of Eudragit L and 5 parts by weight of Witepsol H32 in 50 parts by weight of ethanol and 20 parts by weight of water and are applied to 20 parts by weight of Aerosil, while the solvent is subsequently evaporated. In water, a pleasant solution without a bitter taste is obtained; the certainty of low release after 2 minutes and higher release after 15 minutes has improved.

EXAMPLE 7:

In various formulations of codeine, even together with other active ingredients, its bitter taste is extremely disturbing. In theory, codeine could be processed in the same way as the diclophenac mentioned in Examples 5 and 6. However, another procedure has proved more expedient here:
1 part by weight of codeine base is dissolved with 1 part by weight of Eudragit S and 1 part by weight of Eudragit L in 20 parts by weight of alcohol. The solution is applied to 100 parts by weight of granulated mannitol (having a particle size of 0.2 to 0.4 mm) and the solvent is evaporated, preferably while stirring in vacuo in order to prevent distribution differences. The end product is sieved through a 1 mm sieve, it being necessary to use 13 parts by weight of the mixture in an effervescent tablet for the subsequent dose of 1 part by weight of codeine base. In the effervescent drink, the codeine has completely lost its bitterness and is nevertheless released after 15 to 20 minutes at 37° C.

EXAMPLE 8:

The procedure is as in Example 7, except that 26.6 parts by weight of 74% codeine phosphate are dissolved with 5 parts by weight of Eudragit L, 7.5 parts by weight of Witepsol H32 and 2.5 parts by weight of polysorbate (for better suspension) in a mixture of 100 parts by weight of water, 100 parts by weight of ethanol, 100 parts by weight of acetone and 100 parts by weight of isopropanol and are applied to 20 parts by weight of Aerosil. The solvent is then evaporated. As a result, the certainty of a low release of the codeine after 2 min and a high release after 15 min is improved.

From the various Examples, it can be seen that the amount of matrix and the composition thereof which must be used in order to achieve the suitable masking or release are very dependent on the active ingredient and on the carrier.

We claim:

1. Pharmaceutical formulation in the form of an effervescent or disintegrating tablet or of instant granules, containing at least one active ingredient having an irritating taste and at least one matrix which delays the release of the active ingredient and which contains at least one fatty ester or one wax, characterised in that the matrix is present as an intimate mixture with the active ingredient particles and covers said particles and is applied to a carrier, the formulation releasing at most 65% of the active ingredient in aqueous solution at room temperature within about 2 min but more than 70% of the active ingredient within max. 20 min in 0.1N HCl at 38° C.

2. Formulation according to claim 1, characterized in that it contains 20 to 40 parts by weight of said carrier per part by weight of said active ingredient/matrix mixture or particles.

3. Formulation according to claim 1, characterised in that the matrix contains at least one cellulose derivative.

4. Formulation according to claim 1, characterised in that the carrier comprises at least one member selected from the group consisting of the substances mannitol, sorbitol, sucrose, lactose, silia, starch, polyvinylpyrrolidone, and a component of an effervescent system comprising a combination of an acid and an alkali.

5. Formulation according to claim 1, characterised in that the active ingredient is present in an amount of less than 60 mg and the matrix is present in an amount of 1 to 10 times the amount of active ingredient per tablet or granule dose.

6. Formulation according to claim 1, for an active ingredient for the treatment of diarrhoea, characterised in that it additionally contains a mixture which serves to compensate the electrolyte loss in the body and an amount of alkali metal and/or alkaline earth metal salts.

7. Formulation according to claim 1, characterised in that the matrix furthermore contains at least one of the substances gluconic acid delta-lactone, citric acid or alkali metal or alkaline earth metal carbonates or bicarbonates.

8. Formulation according to claim 1, characterised in that it contains at least one polymethacrylate.

9. Process for the preparation of a formulation according to claim 1, characterised in that the active ingredient is dissolved with the matrix in a common solvent, the solution is uniformly applied to 10–50 parts by weight based on 1 part by weight of the sum of the active ingredient and matrix of a neutral carrier and is dried, whereupon the granules obtained are mixed with the remaining effervescent or disintegration components and flavours.

10. Formulation according to claim 1, characterized in that the formulation releases at most 50% of the active ingredient in aqueous solution at room temperature within about 2 minutes but at least 80% of the active ingredient within a maximum of 20 minutes in 0.1N HCl at 38° C.

11. Formulation according to claim 2, characterized in that said fatty ester or wax has a melting point between 30° and 45° C.

12. Formulation according to claim 11, characterized in that the melting point is between 32° and 35° C.

13. Formulation according to claim 3, characterized in that the cellulose derivative is selected from the group consisting of hydroxypropylmethyl-cellulose phthalate, cellulose acetate phthalate, cellulose acetate trimellitate or cellulose acetobutyrate.

14. Formulation according to claim 4, characterized in that the effervescent system comprises an edible, organic acid and at least one alkali metal or alkaline earth metal carbonate or bicarbonate.

15. Formulation according to claim 5, characterized in that the active ingredient is present in an amount less than 10 mg and the matrix is present in an amount of 3–5 times the active ingredient per tablet or granule dose.

16. Formulation according to claim 6, characterized in that the active ingredient is loperamide and said salt is an organic salt or chloride.

17. Formulation according to claim 1, characterized in that it contains 10 to 50 parts by weight of said carrier per part by weight of said active ingredient/matrix mixture or particles.

* * * * *